United States Patent [19]
Morrisseau

[11] Patent Number: 5,968,002
[45] Date of Patent: Oct. 19, 1999

[54] ORTHOTIC GARMENT AND METHOD

[76] Inventor: John K. Morrisseau, 2210 19th St., SW., Naples, Fla. 34117

[21] Appl. No.: 09/054,051

[22] Filed: Apr. 2, 1998

[51] Int. Cl.[6] .............................. A61F 13/00; A61B 19/00
[52] U.S. Cl. ................................ 602/62; 602/60; 128/869
[58] Field of Search .............................. 602/1, 5, 23, 26, 602/60–63, 75; 128/845, 846, 882, 869; 2/72, 23, 227, 228

[56] References Cited

U.S. PATENT DOCUMENTS

| | | |
|---|---|---|
| 4,601,066 | 7/1986 | Campbell ...................................... 2/70 |
| 5,054,127 | 10/1991 | Zevchak ...................................... 2/247 |
| 5,107,827 | 4/1992 | Boyd ......................................... 602/58 |
| 5,154,691 | 10/1992 | Box et al. ................................... 602/5 |
| 5,267,928 | 12/1993 | Barile et al. ............................. 482/124 |
| 5,358,470 | 10/1994 | Johnson . | 
| 5,397,298 | 3/1995 | Mazza et al. ............................. 602/75 |
| 5,628,725 | 5/1997 | Ostergard . | |

*Primary Examiner*—Richard J. Apley
*Assistant Examiner*—Denise Pothier

[57] ABSTRACT

An orthotic garment (1, 5, 6, 7, 8, 9) has adhesion bases (2) on injury-protective portions of the orthotic garment, injury-protective strips of material (3) attached selectively to the adhesion bases, and a body-protective wrapper such as webbing (4), an injury-covering strap (13) or tape (11) that is fastened selectively to an outside periphery of the garment on an injured portion of a person's body. A method includes determining advantageous support for an injury on a person; providing a garment that fits onto an injured portion of the person and has adhesion bases on injury-protective portions of the orthotic garment; attaching injury-protective strips of material to the adhesion bases; positioning the orthotic garment on the injured portion of the person and wrapping an outside periphery of the orthotic garment selectively to protect the injury.

1 Claim, 3 Drawing Sheets

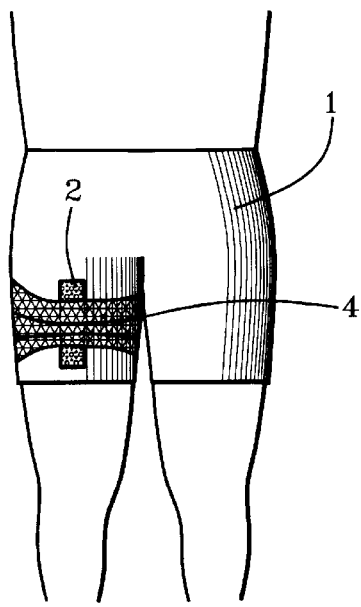
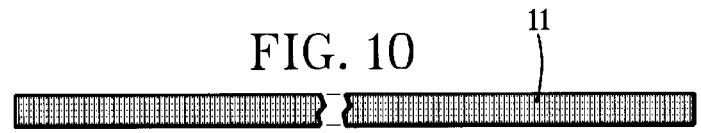
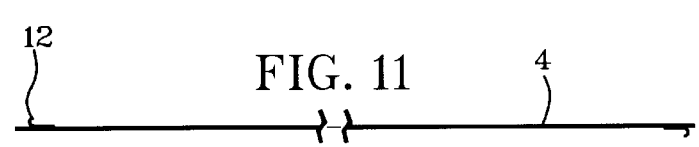
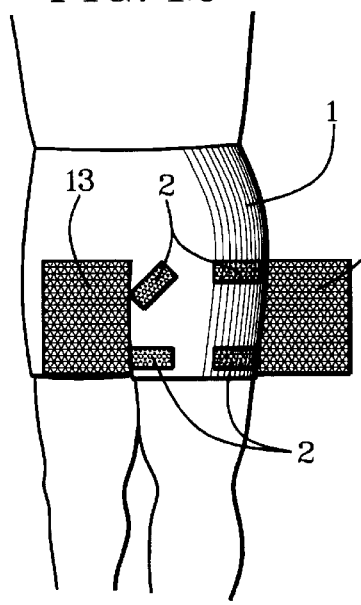
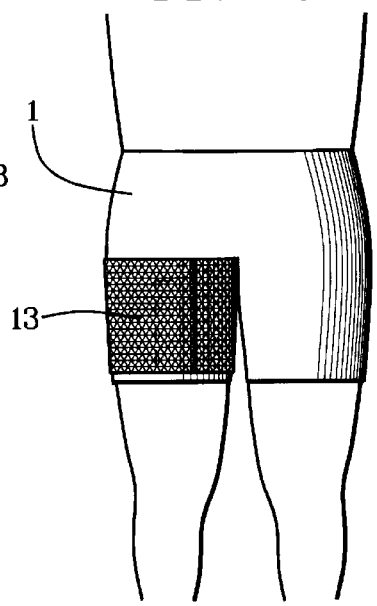
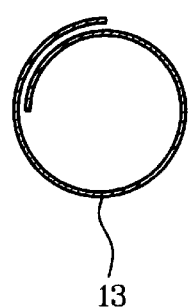

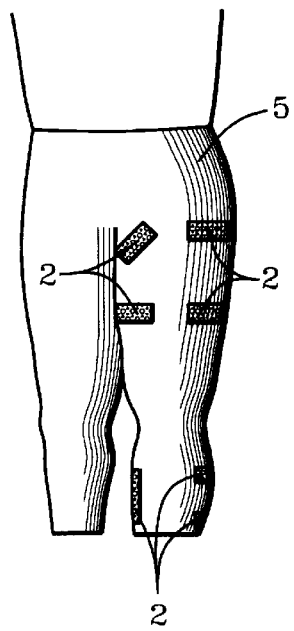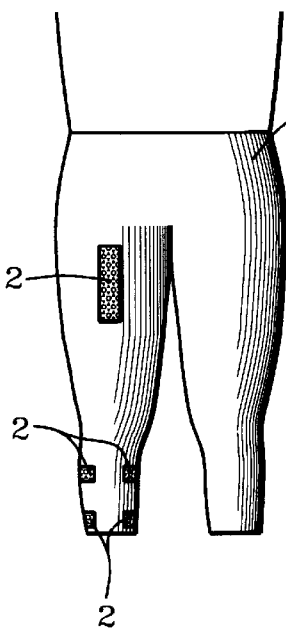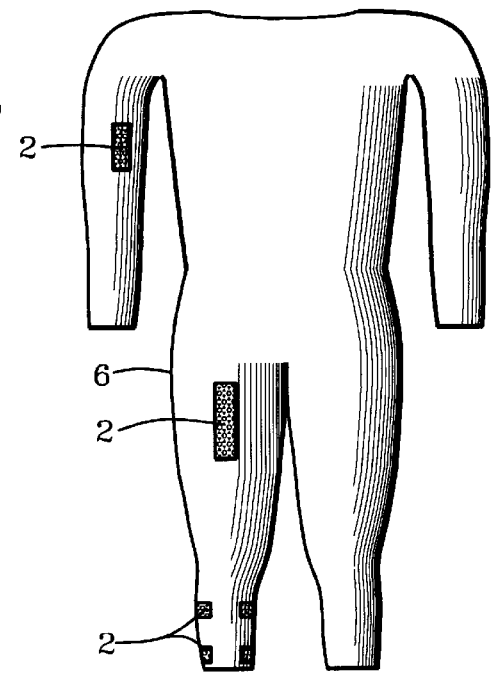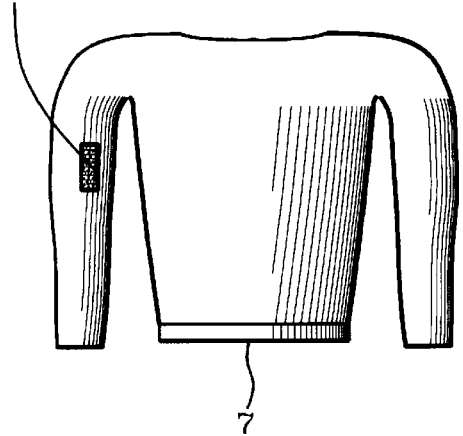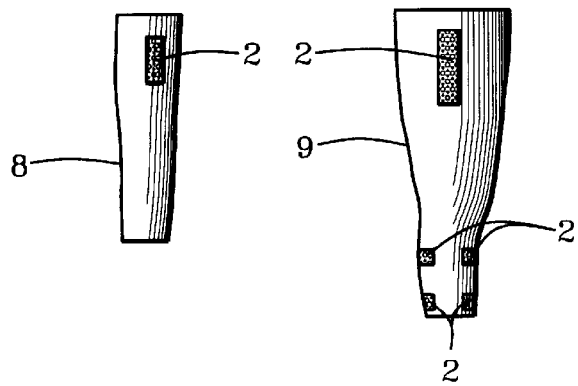

ORTHOTIC GARMENT AND METHOD

BACKGROUND OF THE INVENTION

1. Field of the Invention

This invention relates to orthotics and in particular to support of ruptured muscles, related tendons and joints with webbing-bound garments or parts of garments for specific orthotic support.

2. Relation To Prior Art

Torn or ruptured muscles from sports, exercising, work or accidents are wrapped with webbing for professional orthotic support. Specifically injured portions of particular muscles, tendons and joints are not supported with sufficient precision and accuracy to maximize benefit of orthotic support by wrapping general areas, however. Tear of an upper-leg muscle, for instance, is a frequent rupture that is not supported adequately by general-area wrapping with webbing. Instead of general-area wrapping, this type of rupture and most others also require precision support of ruptured portions and then progressively general wrapping for body protection in appropriate directions of support.

There are no known garment-related orthotic supports that are adaptive to support particular injuries in a manner taught by this invention.

Examples of different but related orthotic supports are described in the following patent documents. U.S. Pat. No. 5,628,725, issued to Ostergard, is limited to a method for using a chest garment with an arm portion and an elastic strap under the axilla of an injured shoulder of an athlete.

U.S. Pat. No. 5,358,470, issued to Johnson, is limited to a shoulder-restricting harness that was attached to a front and a back of an elastic belt.

Problems with treating ruptured muscles, tendons and joints efficiently, expeditiously, conveniently and inexpensively continue to exist, however.

SUMMARY OF THE INVENTION

In light of these problems, objects of patentable novelty and utility taught by this invention are to provide an orthotic garment and method which:

Can be constructed from a garment or part of a garment of an injured individual or from a garment or part of a garment that fits the injured individual;

Can be wrapped precisely to support an injury accurately for effective healing;

Can be removed conveniently after adequate healing;

Can be replaced and adjusted to healing conditions conveniently and appropriately;

Is highly adaptive to types, positions and extents of injuries for all sizes of persons; and Is inexpensive to produce and to use.

This invention accomplishes these and other objectives with an orthotic garment having adhesion bases on injury-protective portions of the garment, injury-protective strips of material attached selectively to the adhesion bases, and a body-protective wrapper such as webbing, a wide resilient strap or tape that fastens selectively to an outside periphery of the garment on an injured portion of a person's body. A method includes determining advantageous support for an injury on a person; providing a garment that fits onto an injured portion of the person and has adhesion bases on injury-protective portions of the garment; attaching injury-protective strips of material to the adhesion bases; positioning the garment on the injured portion of the person and wrapping an outside periphery of the garment selectively to protect the injury.

BRIEF DESCRIPTION OF DRAWINGS

This invention is described by appended claims in relation to description of a preferred embodiment with reference to the following drawings which are described briefly as follows:

FIG. 7 is a rear view showing webbing having been wrapped onto the FIG. 4 illustration;

FIG. 8 is a partially cutaway top view of a body-protective wrapper that is webbing with VELCRO on ends for adhesive wrapping;

FIG. 9 is a partially cutaway top view of a body-protective wrapper that is webbing without attachment means in order to permit use of a selection of end1 adhesion means such as tape and hooks;

FIG. 10 is a partially cutaway top view of a body-protective wrapper that is tape which is preferably adhesive to the adhesion bases but not to garment material;

FIG. 11 is a partially cutaway side view of a body-protective wrapper having hooks at ends for attachment;

FIG. 12 is a front view of an athletic-shorts embodiment of an orthotic garment having a wide, injury-covering strap for wrapping-attachment to the adhesion bases proximate a targeted injury;

FIG. 13 is the FIG. 12 illustration with the injury-covering strap in wrapped mode;

FIG. 14 a top view of the injury-covering strap of FIGS. 12–13;

FIG. 15 is a front view of an orthotic garment that is waist-length tights that fit upper and lower legs where injuries may occur;

FIG. 16 is a rear view of the FIG. 15 illustration;

FIG. 17 is a rear view of a full-body orthotic garment;

FIG. 18 is a rear view of a sweater-shaped orthotic garment;

FIG. 19 is a rear view of an arm-fitting orthotic garment; and

FIG. 20 is a rear view of a leg-fitting orthotic garment.

DESCRIPTION OF PREFERRED EMBODIMENT

Figure 1:
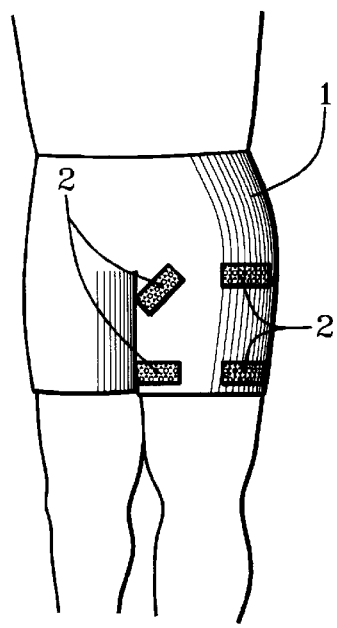
FIG. 1 is a front view of an athletic-shorts embodiment of an orthotic garment having front adhesion bases.

Terms used to describe features of this invention are listed below with numbering in the order of their initial use with reference to the drawings. These terms and numbers assigned to them designate the same features wherever used throughout this description.

1. Shorts-like orthotic garment
2. Adhesion bases
3. Injury-protective strips of material
4. Webbing
5. Tights-like orthotic garment
6. Body-fitting orthotic garment
7. Sweater-like orthotic garment
8. Arm-like orthotic garment
9. Leg-like orthotic garment
10. VELCRO surfaces
11. Adhesive tape
12. Hooks
13. Injury-covering strap Reference is made first to FIGS. 1–7. A shorts-like orthotic garment 1 has adhesion bases 2 to which injury-protective strips of material 3 and webbing 4 as a body-protective wrapper are attached selectively on injury-protective portions of the orthotic garment 1. The adhesion bases 2 are positioned selectively as appropriate for positioning the injury-protective strips of material 3 and body-protective wrapper such as webbing 4.

Figure 2:
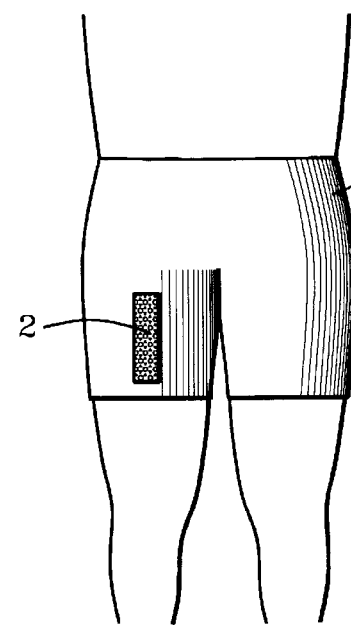
FIG. 2 is a rear view of an athletic-shorts embodiment of an orthotic garment having front adhesion bases.
Figure 3:
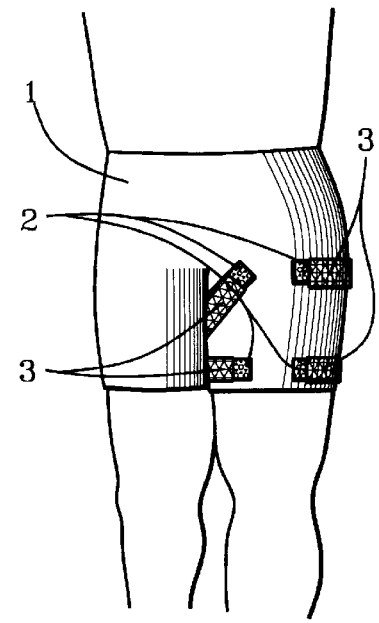
FIG. 3 is a front view of an athletic-shorts embodiment of an orthotic garment with injury-protective strips of material adhered to the front adhesion bases.
Figure 4:
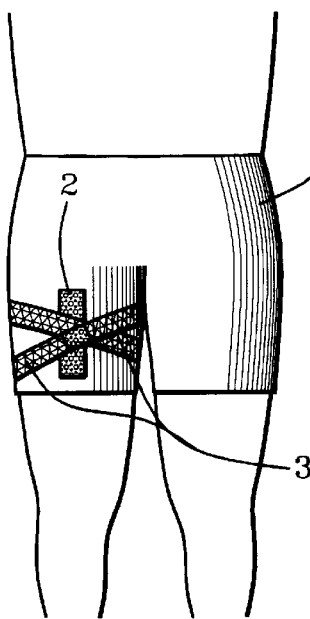
FIG. 4 is a rear view of an athletic-shorts embodiment of an orthotic garment with injury-protective strips of material adhered to the rear adhesion base.
Figure 5:
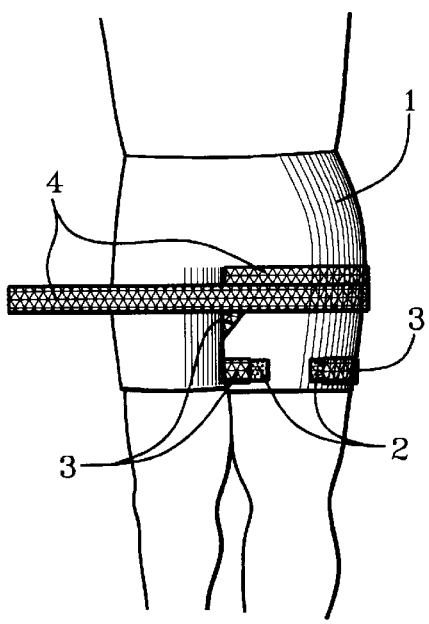
FIG. 5 is a front view showing webbing being wrapped onto the FIG. 3 illustration.

In FIGS. 1, 3, 5 and 12, the adhesion bases 2 are positioned on sides of an upper leg muscle and in FIGS. 2, 4 and 7 the adhesion bases 2 are positioned on a back of a leg of a shorts-like orthotic garment at a position oppositely disposed from the upper leg muscle. This allows the protective strips of material 3 to have a spreading effect on the upper leg muscle by tight attachment between the back position on the leg as shown in FIG. 4 and the front position at sides of the upper leg muscle as shown in FIG. 3.

Reference is made to FIGS. 1–20 in relation to use of this orthotic garment. First, appropriate treatment of an injury to a muscle or a joint is determined. Appropriate treatment can be spreading laterally or linearly or compressing laterally or linearly close to the injury with the injury-protective strips of material 3 and then wrapping for broader body protection with body-protective wrapping such as webbing 4.

A shape and size of orthotic garment having adhesion bases 2 positioned for the appropriate treatment is selected and fit onto a person having such injury. The shape of orthotic garment can be the shorts-like orthotic garment 1 shown in FIGS. 1–7 and 12–13, a tights-like orthotic garment 5 shown in FIGS. 15–16, a body-fitting orthotic garment 6 shown in FIG. 17, a sweater-like orthotic garment 7 shown in FIG. 18, an arm-like orthotic garment 8 shown in FIG. 19 or a leg-like orthotic garment 9 shown in FIG. 20.

After fitting a selected orthotic garment onto an injured person over their injury, the injury is wrapped either without the injury-protective strips of material 3 for some injuries as shown in FIGS. 12–13 or after affixing the injury-protective strips of material as shown in FIGS. 3–7.

Figure 6:
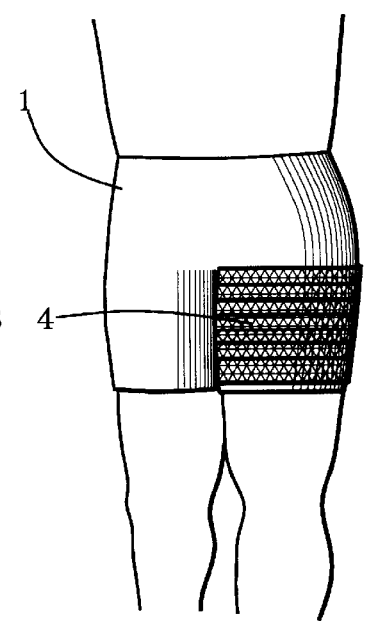
FIG. 6 is a front view showing webbing having been wrapped onto the FIG. 5 illustration.

For particular types of muscle or joint injuries, the body-protective wrapper can be either the webbing 4 shown in FIGS. 5–9 and can have or not have VELCRO surfaces 10 shown in FIG. 8 for attachment to the adhesion bases 2 and for attachment of ends of wrapping shown in FIG. 6. In lieu of VELCRO 10 and other means for attachment of ends of wrappings, adhesive tape 11 can be used. Particular types of adhesive tape 11, shown in FIG. 10, also can be used in lieu of webbing 4 as a body-protective wrapper. Ends of webbing 4 can be attached with hooks 12, shown in FIG. 11, that are sufficiently thin and small.

For some types of injuries, the body-protective wrapper can be an injury-covering strap 13 that is wide and resilient for attachment directly to the adhesion bases 2 as shown in FIGS. 12–14. Use of the injury-protective strips of material 3 is optional for particular types and locations of injuries.

For treating frequently ruptured upper leg muscles, a typical shorts-like orthotic garment 1 fits a person proximate an injury to an upper leg muscle and has adhesion bases 2 with VELCRO surfaces 10 as shown in FIGS. 1–7. Four rectangular adhesion bases 2 are affixed to a front of a leg of the shorts-like orthotic garment 1 with two of the rectangular adhesion bases 2 being proximate oppositely disposed sides of and above and two being proximate oppositely disposed sides of and below a ruptured portion of the upper leg muscle. One rectangular adhesion base 2 is affixed to a back of the leg of the shorts-like orthotic garment 1 at a position oppositely disposed from the four rectangular adhesion bases 2.

The injury-protective strips of material 3 are strips of webbing 4 to which strips of VELCRO 10 are affixed for adherence to the adhesion bases 2. A first of the strips of webbing 4 has a first end that is VELCRO-attached to a rectangular adhesion base 2 on the shorts-like orthotic garment 1 proximate an inside top of the upper leg muscle, a central portion that is VELCRO-attached to the rectangular adhesion base 2 on the back of the leg of the shorts-like orthotic garment 1 and a second end that is VELCRO-attached to a rectangular adhesion base 2 on the shorts-like orthotic garment 1 proximate an outside bottom of the leg muscle. A second of the strips of webbing 4 has a first end that is VELCRO-attached to a rectangular adhesion base 2 on the shorts-like orthotic garment 1 proximate an inside bottom of the upper leg muscle, a central portion that is VELCRO-attached to the rectangular adhesion base 2 on the back of the leg of the shorts-like orthotic garment 1, and a second end that is VELCRO-attached to a rectangular adhesion base 2 on the shorts-like orthotic garment 1 proximate an outside top of the leg muscle. The first of the strips of webbing 4 and the second of the strips of webbing 4 are crossed over the rectangular adhesion base 2 on the back of the leg of the shorts-like orthotic garment 1.

The body-protective wrapper is a strip of webbing 4 that is wrapped onto the leg of the shorts-like orthotic garment 1 at a position external to the upper leg muscle.

A new and useful orthotic garment and method having been described, all such foreseeable modifications, adaptations, substitutions of equivalents, mathematical possibilities of combinations of parts, pluralities of parts, applications and forms thereof as described by the following claims and not precluded by prior art are included in this invention.

What is claimed is:

1. An orthotic garment comprising:

at least one garment sized to fit onto an injured portion of a person;

adhesion bases on injury-protective portions of the at least one garment;

injury-protective strips of material attachable selectively to the adhesion bases;

a body-protective wrapper that is fastened selectively to an outside periphery of the at least one garment sized to fit onto the injured portion of the person's body;

the at least one garment is a shorts type orthotic garment sized to fit the person proximate an injury to an upper leg muscle;

the adhesion bases have readily detachable hook-and-eye adhesion surfaces and include a first, second, third and fourth rectangular adhesion base affixed to a front of a leg of the shorts type orthotic garment with two of the rectangular adhesion bases sized to be proximate oppositely disposed sides of and above and the other two rectangular adhesion bases sized to be proximate oppositely disposed sides of and below a ruptured portion of the upper leg muscle and a fifth adhesion base affixed to a back of the leg of the shorts type orthotic garment at a position oppositely disposed from the first, second, third and forth adhesion bases;

the injury-protective strips of material are webbing and include strips of readily detachable hook-and-eye material affixed to the adhesion bases, wherein the injury-protective strips of material include:

a first of the strips of webbing having a first end that is readily detachable hook-and-eye material attached to said first rectangular adhesion base sized and configured to be on the shorts type orthotic garment proximate an inside top of the upper leg muscle, a central portion that is readily detachable hook-and-eye material attached to said fifth rectangular adhesion base on the back of the leg of the shorts type orthotic garment and a second end that is readily detachable hook-and-eye material attached to said second rectangular adhesion base on the shorts type orthotic garment sized and configured to be proximate the outside bottom of the leg muscle and a second of the strips of webbing having a first end that is readily detachable hook-and-eye material attached to said third rectangular adhesion base on the shorts type orthotic garment sized and configured to be proximate an inside bottom of the leg muscle, a central portion that is readily detachable hook-and-eye material attached to the fifth rectangular adhesion base on the back of the leg of the shorts type orthotic garment, and a second end that is readily detachable hook-and-eye material attached to the fourth rectangular adhesion base on the shorts type orthotic garment sized and configured to be proximate the outside top of the leg muscle;

the first of the strips of webbing and the second of the strips of webbing being crossed over the fifth rectangular adhesion base on the back of the leg of the shorts type orthotic garment, and the body-protective wrapper is a strip of webbing that is sized to wrap onto to the leg of the shorts type orthotic garment at a position external to the upper leg muscle.

* * * * *